United States Patent
Fisher et al.

[11] Patent Number: 5,093,355
[45] Date of Patent: Mar. 3, 1992

[54] BENZYLPYRROLIDINE DERIVATIVES AS DOPAMINE AGONISTS

[75] Inventors: Lawrence E. Fisher; Joan M. Caroon, both of Mountain View; Joseph M. Muchowski, Sunnyvale; Roberto P. Rosenkranz, Menlo Park; Deborah L. McClelland, Palo Alto, all of Calif.

[73] Assignee: Syntex (U.S.A.) Inc., Palo Alto, Calif.

[21] Appl. No.: 726,116

[22] Filed: Jun. 24, 1991

Related U.S. Application Data

[63] Continuation of Ser. No. 428,577, Oct. 30, 1989, abandoned.

[51] Int. Cl.⁵ .................... A61K 31/40; C07D 207/09
[52] U.S. Cl. ................................. 514/428; 514/408; 548/569; 548/578
[58] Field of Search .................. 514/408, 428; 548/569

[56] References Cited

U.S. PATENT DOCUMENTS 4,342,692  8/1982  Suh et al. ........................ 548/570
4,613,606  9/1986  Clark et al. ...................... 546/145

FOREIGN PATENT DOCUMENTS 0294973  12/1988  European Pat. Off.
2733753   2/1978  Fed. Rep. of Germany.

Primary Examiner—Mary C. Lee
Assistant Examiner—Jacqueline Haley
Attorney, Agent, or Firm—Derek P. Freyberg

[57] ABSTRACT

Dopamine agonist compounds disclosed are useful in treating hypertension and congestive heart failure in mammals. The compounds have the following general formula (I)

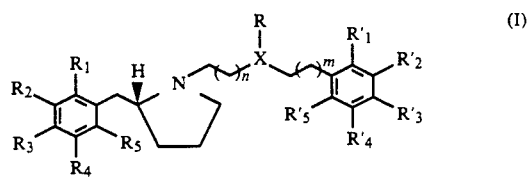

wherein:
X is nitrogen or CH;
R is hydrogen or lower alkyl;
$R_1$, $R'_1$, $R_2$, $R'_2$, $R_3$, $R'_3$, $R_4$, $R'_4$, $R_5$ and $R'_5$ are each independently hydrogen,

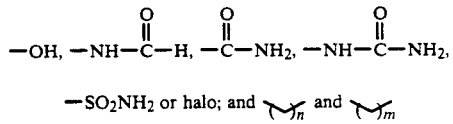

—SO$_2$NH$_2$ or halo; and $\sim\!\!\!\!\gamma_n$ and $\sim\!\!\!\!\gamma_m$ respectively represent —(CH$_2$)$_n$— and (CH$_2$)$_m$ wherein n and m are each independently an integer of from 1 to 10 and pharmaceutically acceptable salts, S stereoisomers and racemic and non-racemic mixtures thereof.

32 Claims, No Drawings

BENZYLPYRROLIDINE DERIVATIVES AS DOPAMINE AGONISTS

This is a continuation of our co-pending application Ser. No. 07/428,577, filed Oct. 30, 1989, now abandoned.

BACKGROUND OF THE INVENTION

1. Field of the Invention

The invention relates generally to dopamine agonists and more particularly to benzylpyrrolidine derivatives which act as dopamine agonists and as such are useful in the treatment of hypertension, congestive heart failure, acute and chronic renal failure, angina and hyperprolactenemia in mammals. The invention also relates to methods of making such compounds, pharmaceutical dosage forms comprising such compounds and to methods of treatment involving the administration of such compounds to a mammal.

2. Background of the Invention

Drugs having the pharmacological effect of dopamine are referred to as dopaminergic agonists in that dopamine is the only marketed sympathomimetic with significant dopaminergic actions in the periphery; some sympathomimetics appear to act on dopamine receptors in the central nervous system. In the periphery, dopamine receptors are prominent in the splanchnic and renal vascular beds, where they mediate vasodilatation. Dilation in these beds is important in the treatment of shock and acute heart failure, since these beds are often critically constricted in these conditions. Dopamine is used in the management of these disorders. It may also be used to induce diuresis, probably consequent to renal vasodilatation, at least in part.

DOPAMINE HYDROCHLORIDE 1,2-Benzenediol,4-(2-aminoethyl-, hydrochloride; Intropin (Arnar-Stone)

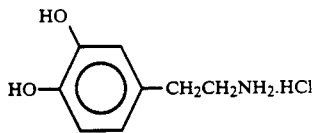

3,4-Dihydroxyphenethylamine Hydrochloride $C_8H_{11}NO_2HCl$ (189.64)

Preparation

Dopamine, which is 3-hydroxytyramine, may be prepared from tyramine by successive nitration to 3-nitrotyramine, reduction to 3-aminotyramine by catalytic hydrogenation, and diazotization to 3-hydroxytyramine.

Description

Dopamine hydrochloride occurs as a white, crystalline powder; decomposes at about 241° C. To avoid oxidation of dopamine hydrochloride injection, the air in containers is replaced with nitrogen. Yellow or brown discoloration of solutions indicates decomposition of the drug, and such solutions should not be used.

Solubility

Freely soluble in water; soluble in alcohol; practically insoluble in chloroform and ether.

Uses

Dopamine is a natural catecholamine formed by the decarboxylation of 3,4-dihydroxyphenylalanine (DOPA). It is a precursor to norepinephrine in noradrenergic nerves and is also a neurotransmitter in certain areas of the central nervous system, especially in the nigrostriatal tract, and in a few peripheral sympathetic nerves.

In the central nervous system and the mesenteric, coronary and renal vascular beds, it acts upon dopamine receptors that are distinct from alpha- and beta-adrenoreceptors. At these dopamine receptors, haloperidol is an antagonist. In the above-named vascular beds it causes vasodilatation. The renal vasodilatation may be one stimulus for diuresis. Dopamine also has moderate $beta_1$- and weak alpha-agonist activities. During a low rate of intravenous infusion, only vasodilatation in the mesenteric, coronary and renal vascular beds usually predominates, and hypotension sometimes occurs. At an intermediate rate of infusion, the heart rate and force of contraction are increased, as is cardiac output, and blood pressure may increase accordingly. At high rates of infusion, alpha-adrenergic vasoconstriction in the mesenteric, coronary and renal vascular beds may overcome the dopaminergic vasodilatation in some recipients.

Dopamine is used in the treatment of shock, for which it has several advantages. Firstly, vasodilatation can often be effected in the two organs most likely to suffer ischemic damage in shock (kidney and small bowel); blood may be moved from the skeletal muscle to more vital organs, cardiac stimulation improves a usually deteriorated cardiac function, and diuresis also helps to preserve renal function. Although dopamine is now the vasopressor agent of choice in shock, a substantial fraction of cases nevertheless fail to respond. Dopamine is also used to treat acute heart failure; the decreased vascular resistance decreases the cardiac afterload, the cardiostimulatory actions improve cardiac output, and the diuresis lessens edema.

U.S. Pat. No. 4,613,606 issued Sept. 23, 1986 discloses a number of tetrahydroisoquinoline derivatives which are indicated as being calcium channel blockers and as such useful for the treatment of cardiovascular disorders including angina, hypertension and congestive heart failure.

European Patent Application No. 0,294,973 published Dec. 14, 1988 discloses a number of dopamine-beta-hydroxylase inhibitors (DBH inhibitors). Dopamine is hydroxylated to norepinephrine by (DBH) in the presence of oxygen and ascorbic acid. There are a number of known DBH inhibitors discussed in 0,294,973 which are believed to be effective in treating hypertension. Methods of synthesizing the novel compounds are also disclosed.

SUMMARY OF THE INVENTION

A primary object of the present invention is to disclose and provide novel compounds represented by the following general structural formula (I):

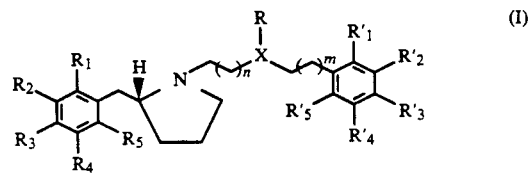

wherein:
X is nitrogen or CH;

R is hydrogen or lower alkyl;

$R_1$, $R'_1$, $R_2$, $R'_2$, $R_3$, $R'_3$, $R_4$, $R'_4$, $R^5$ and $R'_5$ are each independently hydrogen,

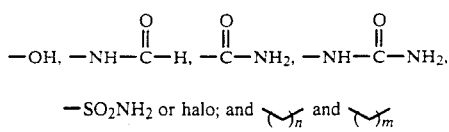

—SO$_2$NH$_2$ or halo; and $\overbrace{\phantom{xx}}_n$ and $\overbrace{\phantom{xx}}_m$ respectively represent —(CH$_2$)$_n$— and (CH$_2$)$_m$ wherein n and m are each independently an integer of from 1 to 10 and pharmaceuatically acceptable salts, S stereoisomers and reacemic and non-racemic mixtures thereof.

In formula I each $R_1$, $R'_1$, $R_4$, $R'_4$, $R_5$ and $R'_5$ is preferably hydrogen each of $R_2$, $R'_2$, $R_3$ and $R'_3$ are preferably hydrogen or —OH with most preferably at least three —OH groups being present on the molecule, R is preferably an ethyl moiety, n is preferably 5 and m is preferably 1.

The dopamine agonist is preferably in the form of a pharmaceutically acceptable salt of a compound of formula (I) which salt is preferably included in a pharmaceutical dosage form by combining the salt with a suitable carrier system—most preferably a carrier system suitable for oral delivery. A mammal can be treated by administering the compound of formula (I) in its dosage form and thereby obtaining the pharmacological effect of the drug on the mammal.

Another object is to provide racemic and non-racemic mixtures of the compounds of formula (I), i.e. mixtures which include the S stereoisomers in addition to the R configuration shown in formula (I).

Another object of the invention is to disclose and provide novel methods of preparing the compounds of formula (I) and their salts as well as the novel intermediates produced by such methods.

Yet another object is to disclose and provide pharmaceutical compositions and dosage forms containing compounds of formula (I) and their salts and esters with pharmaceutically acceptable non-toxic carriers.

Still another object of the invention is to disclose and provide methods of treating hypertension, congestive heart failure, acute and chronic renal failure, angina and hyperprolactenemia in mammals by administering to the mammals the dosage forms of the invention.

A feature of the present invention is that compounds of formula (I) (which shows the R stereoisomers) and these pharmaceutically acceptable salts are orally active.

Another feature of the present invention is that the compounds of formula (I) can be produced via an efficient process and that the processes disclosed allow for the production of racemic mixtures and optically pure stereoisomers.

An advantage of the present invention is that the compounds of formula (I) are very effective dopamine agonists.

An important advantage of the compounds of this invention is that they can be administered orally to treat hypertension, congestive heart failure, acute and chronic renal failure, anginal and hyperprolactenemia.

These and other objects, advantages and features of the present invention will become apparent to those persons skilled in the art upon reading the details of the various compounds, salts and esters thereof, methods of synthesis, and usage as more fully set forth below.

DEFINITIONS

"Alkyl" means a branched or unbranched saturated hydrocarbon chain containing 1 to 10 carbon atoms, such as methyl, ethyl, propyl, tert-butyl, n-hexyl, 2-methylheptyl, n-octyl and the like, unless otherwise indicated;

"Lower alkyl" means a branched or unbranched saturated hydrocarbon chain containing 1 to 4 carbon atoms, such as methyl, ethyl, propyl, isopropyl, tert-butyl, butyl and the like, unless otherwise indicated.

"Lower alkoxy" means the group —OR wherein R is lower alkyl as herein defined.

"Halo" as used herein denotes fluoro, chloro, bromo, or iodo, unless otherwise indicated.

"Phenyl" as used herein encompasses all possible isomeric phenyl radicals optionally monosubstituted or disubstituted with a substituent selected from the group consisting of lower alkyl, lower alkoxy, hydroxy, trifluoromethyl and halo.

"Phenyl-lower-alkyl" as used herein denotes phenyl as defined herein attached to a lower alkyl group as defined herein.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

"Protecting group" means any suitable chemical group that is commonly used in the practice of organic chemistry to modify one or more of the major functional groups in a molecule for the purpose of selectively performing a chemical reaction at another reactive site in a multifunctional molecule. A protecting group is typically formed in a selective manner and is stable to subsequent reactions on the molecule and is selectively removed by reagents that do not attack the regenerated functional group. Suitable protecting groups for the amino group are carbamates such as methyl carbamates and its derivatives like cyclopropylmethyl, diisopropylmethyl, 9-fluorenylmethyl carbamates and the like, substituted ethyl carbamates such as 2,2,2-trichloroethyl, 2-haloethyl, and the like, substituted propyl and isopropyl carbamates such as 1,1-dimethylpropynyl, 1-methyl-1-phenylethyl and derivatives, isobutyl, t-butyl carbamate, t-amyl carbamate, vinyl and allyl carbamate, phenyl and substituted phenyl carbamate, benzyl carbamate and derivatives such as p-methoxybenzyl, 3,5-dimethoxybenzyl, o- and p-nitrobenzyl, halobenzyl, and the like; amides and their derivatives such as N-acetyl and derivatives like N-dichloracetyl, N-trifluoroacetyl, and the like, substituted N-propionyl derivatives such as N-3-phenylpropionyl and derivatives, N-o-nitrocinnamoyl and the like, cyclic imide derivatives such as N-phthaloyl, N-2,3-diphenylmaleoyl, and the like.

A "leaving group" means a group capable of being displaced by a nucleophile in a chemical reaction, for example chloro, bromo, iodo, sulfonate ester, sulfinate ester, carbamate and the like.

The compounds of this invention possess an asymmetric center and thus can be produced as mixtures of stereoisomers or as individual stereoisomers. The individual stereoisomers may be obtained by using an optically active starting material, by resolving a racemic or non-racemic mixture of an intermediate at some appropriate stage of the synthesis or by resolution of the compound of formula (I). It is understood that the individual stereoisomers as well as mixtures (racemic and non-racemic) of stereoisomers are encompassed by the scope of the present invention. The compounds of this invention possess at least one asymmetric center and thus can be produced as mixtures of stereoisomers or as individual R, S or R,S stereoisomers. The individual enantiomers may be obtained by asymmetric synthesis or by resolving a racemic or non-racemic mixture of an intermediate at some appropriate stage of the synthesis. It is understood that the individual R, S or R,S stereoisomers as well as mixtures of stereoisomers are encompassed by the scope of the present invention.

In connection with the present invention the R or (−) stereoisomer is preferred and is shown in formula (I). The S or (+) stereoisomer has the same structure except that the hydrogen atom shown on the 5 membered pyrrolidine ring is projected in the opposite direction in space.

"LAH" is an abbreviation used for the compound lithium aluminum hydride.

"THF" is an abbreviation used for the compound tetrahydrofurane.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror-images of each other.

"Epimers" are diastereoisomers which differ only in the configuration of one asymmetric center.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in a mammal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

Systems used in naming compounds of the present invention are shown below, using a compound of formula (I) as an example.

A racemic mixture of compounds which includes compounds of formula (I) and their S stereoisomers wherein R is propyl, $R_1$, $R'_1$, $R_4$, $R'_4$, $R_5$ and $R'_5$ are hydrogen, $R_3$, $R'_3$, $R_4$ and $R'_4$ are —OH, X is N, n is 4 and m is 1 is named:

(±)-5-[2-(3,4-dihydroxybenzyl)pyrrolidyl]-pentyl, propyl(3,4-dihydroxyphenethyl)amine.

A compound of formula (I) wherein R is propyl, $R_1$, $R'_1$, $R_4$, $R'_4$, $R_5$ and $R'_5$ are hydrogen, $R_3$, $R'_3$, $R_4$ and $R'_4$ are —OH, X is N, n is 5, and m is 1 is named:

(−)1-(6-(2-(3,4-dihydroxyphenyl)ethyl, propyl amino)hexanyl)-2-R-(3,4-dihydroxyphenyl)pyrrolidine.

A bromine salt of a compound of formula (I) wherein R is propyl, $R_1$, $R'_1$, $R_4$, $R'_4$, $R_5$, $R'_5$ and $R'_3$ are hydrogen, $R_3$, $R_4$ and $R'_4$ are —OH, X is N, n is 4 and m is 1 is named:

(R)-2-(3,4-dihydroxybenzyl)-1-(5-(propyl, 2-(3-hydroxy phenyl)ethyl)amino pentyl) pyrrolidine dihydrobromide.

A bromine salt of a compound of formula (I) wherein R is propyl, $R_1$, $R'_1$, $R_4$, $R'_4$, $R_5$, $R'_5$ and $R'_3$ are hydrogen, $R_3$, $R_4$ and $R'_4$ are —OH, X is N, n is 5 and m is 1 is named:

(R)-2-(3,4-dihydroxybenzyl)-1-(6-(4-hydroxy phenethylproylamino)hexanyl)pyrrolidine dihydrobromide.

A stereo isomer of a halide salt of a compound of formula (I) wherein R is propyl, $R_1$, $R'_1$, $R_5$, $R'_5$, $R_4$, $R'_2$ and $R'_3$ are hydrogen, $R_2$, $R_3$ and $R'_4$ are —OH, X is N, n is 5, and m is 1 is named:

S-(6-[2-(3,4-dihydroxybenzyl)pyrrolidine]hexyl-3'-hydroxyphenylethyl propylamine dihydrohalide.

DETAILED DESCRIPTION OF THE PREFERRED EMBODIMENTS OF THE INVENTION

Before the present dopamine agonist compounds and processes for making and using pharmaceutical compositions containing such are described, it is to be understood that this invention is not limited to the particular compounds, intermediates and processes described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singlar forms "a", "an" and "the" include plural referents unless the context clearly dictates otherwise. Thus, for example, reference to a dopamine agonist compound includes mixtures of such compounds, reference to "the hydrogenating reaction" includes reference to a plurality of hydrogenating reactions, reference to "an ester" includes mixtures of esters and so forth.

METHODS OF PREPARATION

Optically pure compounds such as the R stereoisomers of formula (I) of the present invention are prepared by using a commercially available optically pure starting material to prepare an optically pure intermediate. The following REACTION SCHEME I schematically shows how to make an optically pure "R" intermediate. The "R" intermediate is referred to as compound 8. The compound 8 is used a the starting material in REACTION SCHEME II which results in the production of the optically pure "R" form of a compound of formula (I). The S form and racemic mixture can be obtained in the same manner by starting with the S form or racemic mixture respectively of the starting material.

REACTION SCHEME I
PREPARATION OF OPTICALLY ACTIVE "R" INTERMEDIATE

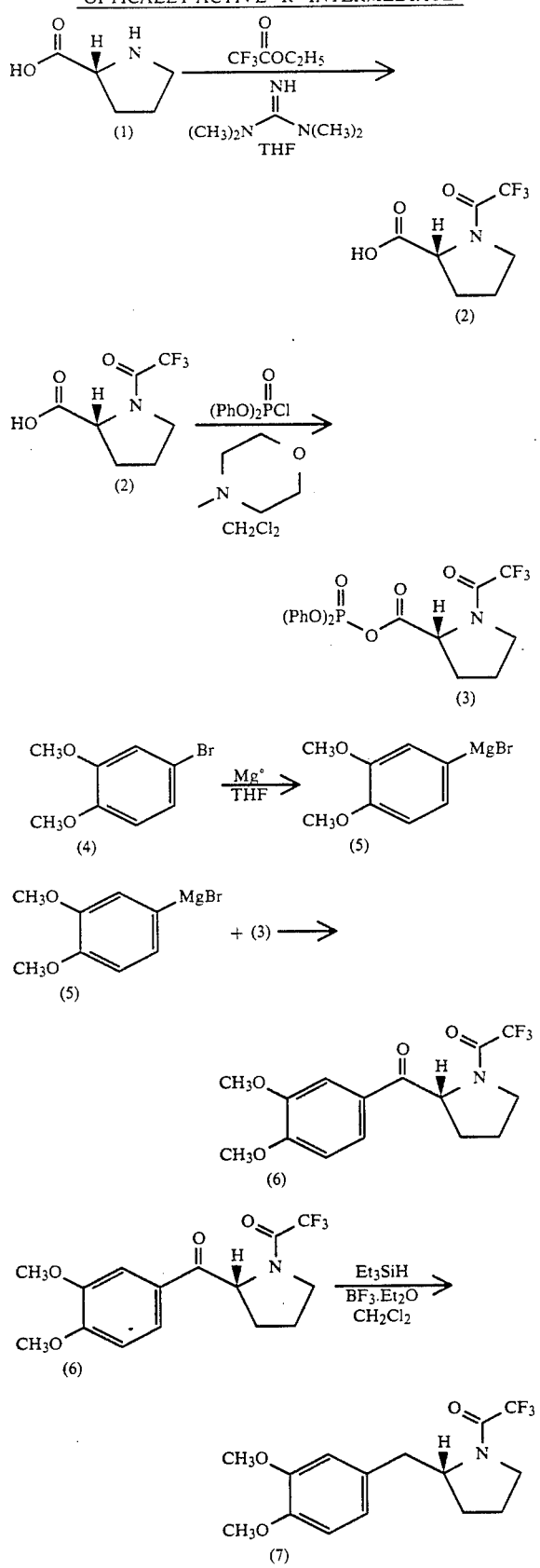

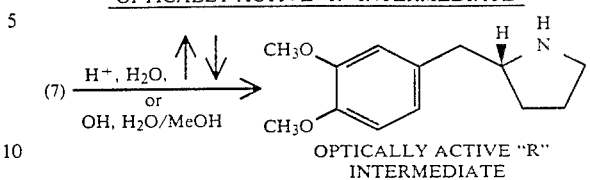

OPTICALLY ACTIVE "R" INTERMEDIATE
(8)

The following includes a description of how the steps of REACTION SCHEME I may be carried out. These techniques are put forth so as to provide those of ordinary skill in the art with a complete disclosure and description of compounds and compositions of the invention and how to carry out the processes of the invention and are not intended to limit the scope of what the inventors regard as their invention. Efforts have been made to insure accuracy with respect to numbers used (e.g. amounts, temperature, etc.) but some experimental errors and deviation should be accounted for. Unless indicated otherwise, parts are parts by weight, temperature is in degrees C and is at room temperature (20° C. to 30°) and pressure is at or near atmospheric.

DESCRIPTION OF REACTION SCHEME I STEPS

Step 1

In a 500 ml round bottom flask was placed 20 g (0.174 moles) 1. (It should be noted that the D-proline (1) can be obtained commercially). To this was added 100 ml dry THF and 50 g (0.34 moles) ethyl trifluoroacetate. The solution/flask was purged with argon and 30 g (0.261 moles) 1,1,3,3-tetramethylguanidine was added dropwise. The solution was allowed to stir until all the D-proline 1 had dissolved (approximately 35 minutes). The solvent was removed in vacuo and the residue dissolved in $CH_2Cl_2$ (200 ml). The solution was washed with 6N HCl (aqueous, 2×100 ml). The organic layer was separated and dried with $Na_2SO_4$, filtered and the solvent removed in vacuo to give an oil which crystallized upon standing. Yield: 29 g, 79% mp, 48°–51° C. The resulting compound 2 is shown in REACTION SCHEME I.

Step 2

29 g 2 (0.137 moles) was dissolved in $CH_2Cl_2$ (300 ml) in a 1 liter round bottom flask and cooled to 0° C. To this solution was added 36.9 g (0.137 moles) diphenyl chlorophosphate followed by 15.27 g (0.151 moles) 4-methylmorpholine. After stirring at 0° C. for 10 minutes, the reaction mixture was allowed to warm to room temperature and stir for an additional 10 minutes. The solution was then diluted with 600 ml dry diethyl ether. After filtration, the filtrate was washed with a saturated solution of $NaHCO_3$ (aq), the organic layer was separated, dried with $MgSO_4$, filtered and the solvent removed in vacuo to give a solid which was hygroscopic and unstable to heat and moisture (90%, 54.8 g). The resulting compound is shown as compound 3 in REACTION SCHEME I.

Step 2A

Reactant for step 3 prepared

To a 250 ml round bottom flask was added 4.51 g (0.186 moles) Mg° turnings and 100 ml dry THF. I$_2$ (one crystal) was added, followed by 27 g (0.124 moles) bromoveratrole dropwise. (The bromoveratrole is shown as compound 4 and can be obtained commercially.) The reaction was heated under reflux after addition of the first few drops of bromoveratrole until the iodine color disappeared. Following this, the remainder of 4-bromoverabrole was added dropwise. A condition of reflux was maintained for 2 hours. The solution was then cooled to room temperature and added to a solution of 54 g (0.123 moles) 3 in 250 ml dry THF at −70° C. The rate of addition was monitored to keep the reaction temperature below −60° C. Once addition was complete the reaction mixture was warmed to room temperature and allowed to stir for 14 hours. It was then poured into a saturated solution of ammonium chloride (500 ml) and shaken. The organic layer was separated and dried with MgSO$_4$, filtered, and the solvent removed in vacuo to give an oil. This oil was subjected to flash chromatography in 1:1 hexane:ethyl acetate to give 20.4g (50%) of a crystalline ketone. mp 121°–123° C. $[\alpha]^D_{25} = 65°$ C. = 1.2(CHCl$_3$)

Step 3

In Step 3' diphenylphosphoric-carboxylic mixed anhydride compound 3 is converted to a ketone 6. Typically the compound 3 is dissolved in an inert solvent as defined above, preferably tetrahydrofuran, and cooled to a temperature of about −100° to −50° C., preferably about −60° C. to −70° C. To the cold solution is added from 1 to 2 molar equivalents, preferably about 1.1 molar equivalents, of a Grignard reagent 5 formed from commercially available 4-bromoveratrole as described above in STEP 2A. The reaction mixture is then allowed to rise to a temperature of about 0° to 30° C., preferably about 25° C., for about 5–30 hours, preferably about 14 hours. When the reaction is substantially complete, compound 6 is isolated and purified by conventional means, preferably chromatography.

Step 4

4.9 g (0.015 moles) 6 was dissolved in 50 ml dry CH$_2$Cl$_2$ in a 500 ml round bottom flask. To the solution was added 20 g (0.172 moles) triethylsilane and 50 ml BF$_3$·Et$_2$O. The reaction mixture was stirred at room temperature for 3 days, after which time a saturated solution of potassium carbonate was added cautiously in a dropwise manner. When no more gas was evolved as a result of addition of K$_2$CO$_3$, 100 ml CH$_2$Cl$_2$ was added. The mixture was shaken. The triphasic mixture was filtered through a fritted glass funnel and the organic layer was separated and dried with MgSO$_4$. Removal of the solvent in vacuo yielded 7 as an oil (3.2 g, 68%) which could be used without further purification.

Step 5

To a solution of 3.2 g (0.010 moles) 7 in 50 ml isopropyl alcohol was added 15 ml of 12.5 M HCl. The mixture was then heated under reflux until all starting material had disappeared (approximately 24 hours). The solvent was removed in vacuo to give an oil which could be recrystallized from isopropyl alcohol-ether to give needles, (2.5 g, 97%), m.p. 165°–167° C. The resulting compound is shown in REACTION SCHEME I as compound 8. The compound 8 is used as a reactant in REACTION SCHEME III described below to produce a compound of formula (I).

REACTION SCHEMES II AND III

Compound 8 is produced as shown and described above regarding REACTION SCHEME I. Compound 8 is used as a reactant in REACTION SCHEME III to produce dopamine agonists of the present invention. To make use of the compound 8 as a reactant, an additional reactant produced by REACTION SCHEME II must be produced. It is the production of this additional reactant which is schematically described below in REACTION SCHEME II.

The steps of REACTION SCHEME II are carried out in order to produce a reactant (shown as structure 12) which can be used with the reactant (structure 8) produced in REACTION SCHEME I. The reactants (8) and (12) are combined in REACTION SCHEME III.

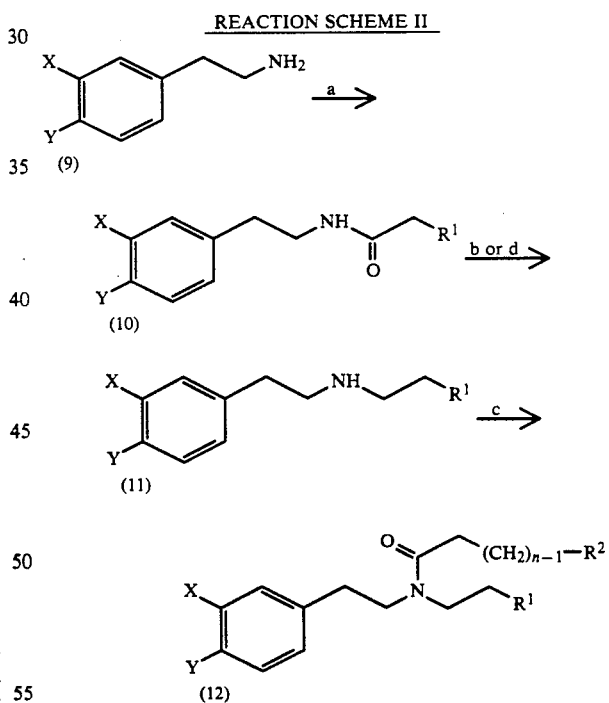

NOTE: The symbols above are defined following REACTION SCHEME III

GENERAL DESCRIPTION OF REACTION SCHEME II

A phenethylamine compound 9 is acrylated to give an amide compound 10. The amide compound 10 is reduced with either LAH or BH$_3$·DMS in a solvent such as THF to yield the alkylated phenethyl amine compound 11. This amine is acylated with a halogenated acid chloride such as 6-bromohexanoyl chloride to give the halogenated amide compound 12.

REACTION SCHEME III

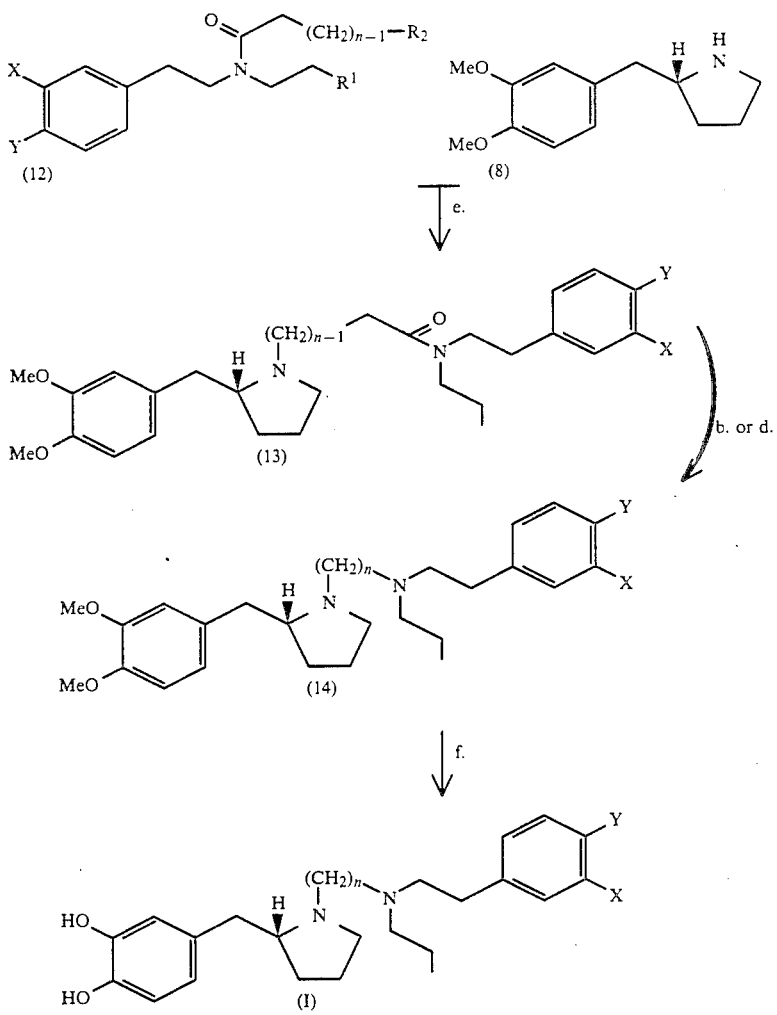

X, Y = H or OMe
R¹ = CH₃ or alkyl
R² = alkyl halide such as CH₂CH₂CH₂Br
n = 1-8
X', Y' = H or OH
a.) R¹CH₂COCl, TEA, CH₂Cl₂
b.) LAH
c.) R²CH₂CH₂COCl, K₂CO₃, H₂O, EtOAc
d.) BH₃.DMS
e.) DMF, TEA, NaI
f.) BBr₃

GENERAL DESCRIPTION OF REACTION SCHEME III

Amide compound 12 is condensed with pyrrolidine compound 8 obtained in REACTION SCHEME I to give compound 13. The compound 13 is produced in REACTION SCHEME II. The compound 13 is then reduced with either LAH or BH₃.DMS to give diamine compound 14. The O-methyl groups are removed by treatment with BBr₃ to give the catecholamine of general structural formula (I).

DETAILED DESCRIPTION OF REACTION SCHEME II STEPS

Step 6

A mixture of 25 ml 4-methoxyphenylethylamine compound 9 (shown above wherein X is H and Y is MeO) (0.17 mol), 25 ml triethylamine, and 250 ml methylenechloride was cooled to 0° C. To this solution was added 17.4 ml propionyl chloride (0.2 mol) dropwise. The mixture was stirred 2 hours. It was then washed with 300 ml 1N HCl followed by saturated NaHCO₃ solution. The organic layer was dried over Na₂SO₄, filtered and the solvent removed under vacuum to give 32.4 g amide (structure 10) (X=H,Y=OMe,R¹=CH₃), as a yellow solid. Recrystallization from Et₂O gave a white solid, mp 114°-116°.

Step 7

Amide 10 (32.4g) in 100 ml THF was added dropwise to a warm (40°-60° C.) solution of 6.5 g LAH in 200 ml THF. After the addition the solution was heated at reflux 3 hours. The mixture was then cooled to room temperature, the excess LAH destroyed by the sequential addition of 6.5 ml water, 7 ml 10% NaOH, and 20 ml of water. The precipitate was removed by filtration, the filter cake washed with ethyl ether, and the filtrate concentrated under vacuum to give a thick oil. The oil was dissolved in isopropanol and acidified with methanolic HCl. The hydrochloride salt of amine 11 precipitated with addition of Et$_2$O, filtered and air dried to give 22 gr white solid, m.p. 197°-200° C.

Step 8

To a cold (0°-5°) solution of 11 g (48 mmol) of compound 11, (N-(4-methoxyphenethyl)n-propylamine hydrochloride) 10 gr K$_2$CO$_3$, 200 ml H$_2$O, and 300 ml Et$_2$O Ac was added dropwise 10 ml 6-bromohexanoyl chloride (65 mmol). The mixture was stirred 2 hours. The layers were separated, and the organic layer dried over Na$_2$SO$_4$. The drying agent was removed by filtration. The solvent was removed under vacuum to give 14g of a yellow oil (R$_2$=CH$_2$CH$_2$CH$_2$Br) which was shown to be compound 12.

DETAILED DESCRIPTION OF REACTION SCHEME III STEPS

The following STEPS of REACTION SCHEME III explain how reactants 8 and 12 produced in REACTION SCHEMES I and II, respectively, are used to make dopamine agonists of the present invention, i.e., compounds of general structural formula (I).

Step 9

In 50 ml DMF was combined 2 g 2-(3,4-dimethoxybenzyl)pyrrolidine hydrochoride (structure 8), 3 g bromide (structure 12 wherein X is H and Y is MeO), 5 ml triethylamine, 1 gr K$_2$CO$_3$, and 0.1 g NaI. The mixture was heated at 60° C. for 18 hours. Then the mixture was poured into 200 ml ice water. The solution was acidified with conc. HCl and washed with Et$_2$O. The aqueous layer was basified with 10% NaOH solution and the product extracted into EtOAc. The organic layer was dried over Na$_2$SO$_4$, and the solvent removed to yield 2.7 g of compound 13 wherein X is H and Y is MeO.

Step 10

Amide of structure 13 obtained from step 9 was dissolved in 20 ml THF and added slowly to a refluxing solution of 1 g LAH in 150 ml THF. After the addition was complete, the solution was heated at reflux an additional 3 hours, cooled, the excess LAH destroyed with H$_2$O and filtered. Removal of the solvent under vacuum gave a crude compound shown as structure 14 (wherein X is H and Y is MeO) in the form of a thick oil.

Chromatography on silica gel with 3% MeOH in CH$_2$Cl$_2$ gave 1 g of pure diamine of structure 14.

Step 11

The diamine compound 14 (1 g) was dissolved in 20 ml CH$_2$Cl$_2$ and cooled to 0° C., under N$_2$. An excess of 1M BBr$_3$ (15 ml) in a solvent of CH$_2$Cl$_2$ was added and the mixture allowed to warm to room temperature. When the reaction was complete by TLC., the solution was cooled to 0° C. and MeOH added. The solvents were removed under vacuum, MeOH was again added and again the solvent removed at 40° C. under vacuum and dried further at room temperature under vacuum 18 hours. The resulting 0.75 gr pink foam was compound (I) (X'=H, Y'=OH, n=5). $[\alpha]^D_{25} = -5.14$.

REPRESENTATIVE COMPOUNDS

Representative compounds of formula (I) and salts of such compounds are given below. These compounds and their (S) stereoisomers and racemic mixtures thereof could be produced by the process steps described above. The (S) compounds and racemic mixtures are made by changing the D-proline starting material to L-proline or a racemic mixture of (D) and L-proline, respectively. The D-proline gives the (R) or (−) compounds of formula (I) and L-proline gives the (S) or (+) compound.

N-(R)-5-[2-(3,4-dihydroxybenzyl)pyrrolidinyl-pentyl-N-propyl-N-(3',4'-dihydroxyphenethyl)amine N-(R)-6-[2-(3,4-dihydroxybenzyl)pyrrolidinyl-hexanyl-N-propyl-N-(3',4'-dihydroxyphenethyl)amine N-(R)-5-[2-(3,4-dihydroxybenzyl)pyrrolidinyl-pentyl-N-propyl-N-(3',4'-dihydroxyphenethyl)amine dihydrobromide N-(R)-6-[2-(3,4-dihydroxybenzyl)pyrrolidinyl-hexanyl-N-propyl-N-(3',4'-dihydroxyphenethyl)amine dihydrobromide N-(R)-5-[2-(3,4-dihydroxybenzyl)pyrrolidinyl-pentyl-N-butyl-N-(3',4'-dihydroxyphenethyl)amine N-(R)-6-[2-(3,4-dihydroxybenzyl)pyrrolidinyl-hexanyl-N-butyl-N-(3',4'-dihydroxyphenethyl)amine N-(R)-6-[2-(3,4-dihydroxybenzyl)pyrrolidinyl-hexanyl-N-butyl-N-(3',4'-dihydroxyphenethyl)amine dihydrobromide N-(R)-5-[2-(3,4-dihydroxybenzyl)pyrrolidinyl-pentyl-N-propyl-N-(4'-hydroxyphenethyl)amine N-(R)-5-[2-(3,4-dihydroxybenzyl)pyrrolidinyl-pentyl-N-propyl-N-(3'-hydroxyphenethyl)amine N-(R)-5-[2-(3,4-dihydroxybenzyl)pyrrolidinyl-pentyl-N-propyl-N-(4'-hydroxyphenethyl)amine dihydrobromide N-(R)-5-[2-(3,4-dihydroxybenzyl)pyrrolidinyl-pentyl-N-propyl-N-(3'-hydroxyphenethyl)amine dihydrobromide N-(R)-7-[2-(3,4-dihydroxybenzyl)pyrrolidinyl-heptanyl,N-propyl-N-(3',4'-dihydroxyphenethyl)amine N-(R)-6-[2-(3,4-dihydroxybenzyl)pyrrolidinyl-hexanyl-N-propyl-N-(,4'-hydroxyphenethyl)amine N-(R)-5-[2-(3,4-dihydroxybenzyl)pyrrolidinyl-pentyl-N-propyl-N-(3',4'-dihydroxyphenethyl)amine dihydrochloride N-(R)-6-[2-(3,4-dihydroxybenzyl)pyrrolidinyl-hexanyl-N-propyl-N-(3',4'-dihydroxyphenethyl)amine dihydrochloride N-(R)-5-[2-(3,4-dihydroxybenzyl)pyrrolidinyl-pentyl-N-butyl-N-(4'-hydroxyphenethyl)amine N-(R)-6-[2-(3,4-dihydroxybenzyl)pyrrolidinyl-hexanyl-N-butyl-N-(4'-hydroxyphenethyl)amine N-(R)-6-[2-(3,4-dihydroxybenzyl)pyrrolidinyl-hexanyl-N-butyl-N-(4 -hydroxyphenethyl)amine dihydrobromide N-(R)-7-[2-(3,4-dihydroxybenzyl)pyrrolidinyl-heptanyl, N-propyl-N-(4'-hydroxyphenethyl)amine N-(R)-6-[2-(3,4-dihydroxybenzyl)pyrrolidinyl-hexanyl-N-propyl-N-(3'-hydroxyphenethyl)amine N-(R)-5-[2-(3,4-dihydroxybenzyl)pyrrolidinyl-pentyl-N-propYl-N-(4'-hydroxyphenethyl)amine dihydrochloride N-(R)-5-[2-(3,4-dihydroxybenzyl)pyrrolidinyl-pentyl-N-propyl-N-(3'-hydroxyphenethyl)amine dihydrochloride N-(R)-5-[2-(4-hydroxybenzyl)pyrrolidinyl-pentyl-N-propyl-N-(3',4'-dihydroxyphenethyl)amine N-(R)-6-[2-(4-hydroxybenzyl)pyrrolidinyl-hexanyl-N-propyl-N-(3',4'-dihydroxyphenethyl)amine N-(R)-5-[2-(3-hydroxybenzyl)pyrrolidinyl-pentyl-N-propyl-N-(3',4'-dihydroxyphenethyl)amine dihydrobromide N-(R)-6-[2-(3-hydroxybenzyl)pyrrolidinyl-hexanyl-N-propyl-N-(3',4'-dihydroxy phenethyl)amine dihydrobromide N-(R)-5-[2-(4-hydroxybenzyl)pyrrolidinyl-pentyl-N-butyl-N-(3',4'-dihydroxyphenethyl)amine N-(R)-6-[2-(4-hydroxybenzyl)pyrrolidinyl-hexanyl-N-butyl-N-(3',4'-dihydroxyphenethyl)amine N-(R)-6-[2-(4-hydroxybenzyl)pyrrolidinyl-hexanyl-N-butyl-N-(3',4'-dihydroxyphenethyl)amine dihydrobromide

UTILITY AND ADMINISTRATION

The compounds of Formula I and the pharmaceutically acceptable non-toxic esters and salts thereof, are useful in the treatment of hypertension, congestive heart failure, acute and chronic renal failure, angina and hyperprolactenemia in mammals. These compounds can be used both prophylactically and therapeutically.

Pharmaceutical dosage forms which include compositions containing compounds of formula (I) and salts thereof are thus administered to patients suffering from hypertension or congestive heart failure. The compounds act to relieve blood pressure and improve heart action by acting as dopamine agonists. In addition, these compositions may be used to treat other conditions as recognized by those skilled in the art.

Initially, compounds of general structural formula (I) wherein X is N, R is propyl, $R_1$, $R'_1$, $R_4$, $R'_4$, and $R_5$, $R'_5$ are H, $R_2$, $R'_2$ and $R_3$, $R'_3$ are OH, m is 1 and n is 5 were screened for affinity at the D1 and D2 dopamine receptor subtypes via ligand binding techniques. D1 and D2 dopamine receptors in rat striatal membranes were labelled with 0.2 nM [3H]SCH 23390 and 0.2 nM as that level of binding that was not displaced by 1 uM (+)butaclamol. [3H]Spiperone competition studies were done in the presence of 30 nM ketanserin. These compounds, which were examined at concentrations from 0.1 nM to 100 uM, demonstrated high affinity for the D1 and D2 receptor subtypes in these assays.

The compounds were subsequently tested following intra-arterial administration in an in situ renal and femoral arterial preparation in the dog, as developed by L. I. Goldberg, to test for DA1 and DA2 dopamine activity, respectively. Details of the methodology are provided in the European J. Pharmacol. 18:137, 1983, as well as in Hypertension, 6:1–25, 1984. These compounds were found to be highly active when compared to dopamine and di-propyl dopamine, the respective DA1 and DA2 standards for this preparation.

Additionally, these compounds were examined for diuretic activity for 6 hours following oral compound administration in the saline-loaded spontaneously hypertensive rat (SHR). Methods for this assay have been previously described (Rosenkranz, et al, Proc. West. Pharmacol. Soc. 28:87, 1985). The diuretic and natriuretic effects elicited by these compounds were characterized by an immediate onset of action. Over the course of the 6 hour study, these compounds were found to be as efficacious as the standard diuretic agent, hydrochlorothiazide.

Finally, these compounds were screened for oral antihypertensive activity in the conscious restrained rat. Adult male SHR were instrumented for blood pressure and heart rate measurements under light ether anesthesia. The animals were maintained on a plexiglass restraining board following surgery, and were allowed a 1 hour recovery period prior to the oral administration of the test compounds. These compounds were found to decrease blood pressure in the absence of a reflex tachycardia for up to 4 hours post-dosing.

The instant invention is disclosed and described herein in what is considered to be the most practical and preferred embodiments. It is recognized, however, that departures may be made therefrom which are within the scope of the invention, and that obvious modifications will occur to one skilled in the art upon reading this disclosure.

What is claimed is:

1. A compound of the formula

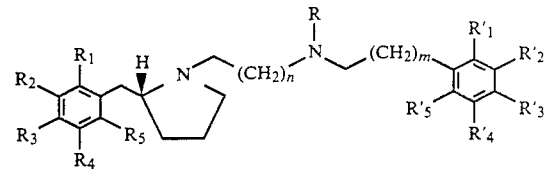

wherein:

R is hydrogen or lower alkyl;

$R_1$, $R'_1$, $R_2$, $R'_2$, $R_3$, $R'_3$, $R_4$, $R'_4$, $R_5$, $R'_5$ are each independently hydrogen, hydroxy, formylamino, aminocarbonyl, (aminocarbonyl)amino, aminosulfonyl, or halo; and n and m are each independently an integer from 1 to 10, or its S stereoisomer, or a racemic mixture of isomers thereof, or a pharmaceutically acceptable salt of the compound, of its S stereoisomer, or of a racemic or non-racemic mixture of isomers thereof.

2. The compound of claim 1 wherein $R_1$, $R'_1$, $R_4$, $R'_4$, $R_5$, and $R'_5$ are hydrogen; and R is lower alkyl of 1 to 4 carbon atoms, or its S stereoisomer, or a racemic or non-racemic mixture of isomers thereof, or a pharmaceutically acceptable salt of the compound, its S stereoisomer, or a racemic or non-racemic mixture of isomers thereof.

3. The compound of claim 2 wherein each of $R_2$, $R'_2$, $R_3$, $R'_3$ is independently hydrogen or hydroxy, or its S stereoisomer, or a racemic or non-racemic mixture of isomers thereof, or a pharmaceutically acceptable salt of the compound, its S stereoisomer, or a racemic or non-racemic mixture of isomers thereof.

4. The compound of claim 3 wherein n is an integer from 3 to 8; and m is an integer from 1 to 3, or its S stereoisomer, or a racemic or non-racemic mixture of isomers thereof, or a pharmaceutically acceptable salt of the compound, its S stereoisomer, or a racemic or non-racemic mixture of isomers thereof.

5. The compound of claim 4 wherein

R is propyl;

n is 4 or 5; and m is 1, or its S stereoisomer, or a racemic or non-racemic mixture of isomers thereof, or a pharmaceutically acceptable salt of the compound, its S stereoisomer, or a racemic or non-racemic mixture of isomers thereof.

6. The compound of claim 5 wherein $R_2$, $R'_2$, $R_3$, and $R'_3$ are hydroxy; and n is 4, namely, R)-2-(3,4-dihydroxybenzyl)-1-[5-(N-(2-(3,4-dihydroxyphenyl)-ethyl)-N-propylamino)pentyl]pyrrolidine
or its S stereoisomer, or a racemic or non-racemic mixture of isomers thereof,
or a pharmaceutically acceptable salt of the compound, its S stereoisomer, or a racemic or non-racemic mixture of isomers thereof.

7. The compound of claim 6 which is (R)-2-(3,4-dihydroxybenzyl)-1-[5-(N-(2-(3,4-dihydroxyphenyl)-ethyl)-N-propylamino)pentyl]pyrroline,
or a pharmaceutically acceptable salt thereof.

8. The compound of claim 7 which is a pharmaceutically acceptable salt of (R)-2-(3,4-dihydroxybenzyl)-1-[5-(N-(2-(3,4-dihydroxyphenyl)ethyl)-N-propylamino) pentyl]-pyrrolidine.

9. The compound of claim 5 wherein
$R_2$, $R'_2$, $R_3$, and $R'_3$ are hydroxy; and
n is 5, namely,
(R)-2-(3,4-dihydroxybenzyl)-1]6-(N-(2-(3,4-dihydroxyphenyl)ethyl)-N-propylamino)hexyl]-pyrrolidine,
or its S stereoisomer, or a racemic or non-racemic mixture of isomers thereof,
or a pharmaceutically acceptable salt of the compound, its S stereoisomer, or a racemic or non-racemic mixture of isomers thereof.

10. The compound of claim 9 which is (R)-2-(3,4-dihydroxybenzyl)-1-[6-(N-(2-(3,4-dihydroxyphenyl)ethyl-N-propylamino)hexyl]pyrrolidine, or a pharmaceutically acceptable salt thereof.

11. The compound of claim 10 which is a pharmaceutically acceptable salt of (R)-2-(3,4-dihydroxybenzyl)-1-[6-(N-(2-(3,4-dihydroxyphenyl)ethyl)-N-propylamino)-hexyl]-pyrrolidine.

12. The compound of claim 5 wherein
$R_2$, $R_3$, and $R'_3$ are hydroxy;
$R'_2$ is hydrogen; and
n is 4, namely,
(R)-2-(3,4-dihydroxybenzyl)-1-[5-(N-(2-(4-hydroxyphenyl)ethyl)-N-propylamino)pentyl]-pyrrolidine,
or its S stereoisomer, or a racemic or non-racemic mixture of isomers thereof,
or a pharmaceutically acceptable salt of the compound, its S stereoisomer, or a racemic or non-racemic mixture of isomers thereof.

13. The compound of claim 12 which is (R)-2-(3,4-dihydroxybenzyl)-1-[5-(N-(2-(4-hydroxyphenyl)ethyl)-N-propylamino)pentyl]pyrrolidine, or a pharmaceutically acceptable salt thereof.

14. The compound of claim 12 which is a pharmaceutically acceptable salt of (R)-2-(3,4-dihydroxybenzyl)-1-[5-(N-(2-(4-hydroxyphenyl)ethyl)-N-propylamino)pentyl]-pyrrolidine.

15. The compound of claim 5 wherein
$R_2$, $R_3$, and $R'_3$ are hydroxy;
$R'_2$ is hydrogen; and
n is 5, namely,
(R)-2-(3,4-dihydroxybenzyl)-1[6-(N-(2-(4-hydroxyphenyl)ethyl)-N-propylamino)hexyl]-pyrrolidine,
or its S stereoisomer, or a racemic or non-racemic mixture of isomers thereof,
or a pharmaceutically acceptable salt of the compound, its S stereoisomer, or a racemic or non-racemic mixture of isomers thereof.

16. The compound of claim 15 which is (R)-2-(3,4-dihydroxybenzyl)-1-[6(N-(2(4-hydroxyphenyl)ethyl)-N-propylamino)hexyl]pyrrolidine, or a pharmaceutically acceptable salt thereof.

17. The compound of claim 16 which is a pharmaceutically acceptable salt of (R)-2-(3,4-dihydroxybenzyl)-1-[6(N-(2(4-hydroxyphenyl)ethyl)-N-propylamino)hexyl]pyrrolidine.

18. A composition, comprising:
a pharmaceutically acceptable carrier; and
a compound of the formula

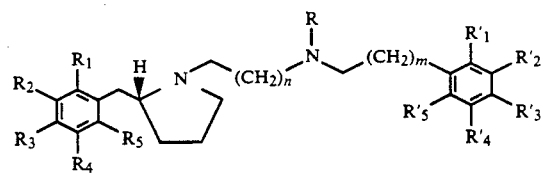

wherein:
R is hydrogen or lower alkyl;
$R_1$, $R'_1$, $R_2$, $R'_2$, $R_3$, $R'_3$, $R_4$, $R'_4$, $R_5$, and $R'_5$ are each independently hydrogen, hydroxy, formylamino, aminocarbonyl, (aminocarbonyl)amino, aminosulfonyl, or halo; and
n and m are each independently an integer from 1 to 10,
or its S stereoisomer, or a racemic or non-racemic mixture of isomers thereof, or a pharmaceutically acceptable salt of the compound, its S stereoisomer, or a racemic or non-racemic mixture of isomers thereof.

19. The composition of claim 18 wherein
$R_1$, $R'_1$, $R_4$, $R'_4$, $R_5$ and $R'_5$ are hydrogen;
each of $R_2$, $R'_2$, $R_3$ and $R'_3$ is independently hydrogen or hydroxy;
R is lower alkyl of 1 to 4 carbon atoms;
n is an integer form 3 to 8; and
m is an integer from 1 to 3.

20. The composition of claim 19 wherein
R is propyl;
n is 4 or 5; and
m is 1.

21. The composition of claim 20 wherein the compound is (R)-2-(3,4-dihydroxybenzyl)-1-[5-(N-(2(3,4-dihydroxyphenyl)ethyl)-N-propylamino)pentyl[pyrrolidine, or a pharmaceutically acceptable salt thereof.

22. The composition of claim 20 wherein the compound is (R)-2-(3,4-dihydroxybenzyl)-1-[6-(N-(2-(4-hydroxyphenyl)ethyl)-N-propylamino)hexyl]pyrrolidine, or a pharmaceutically acceptable salt thereof.

23. A method of treating cardiovascular disorders comprising administering to a mammal in need thereof a pharmaceutically effective amount of a compound of the formula

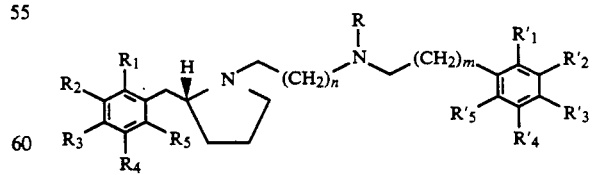

wherein:
R is hydrogen or lower alkyl;
$R_1$, $R'_1$, $R_2$, $R'_2$, $R_3$, $R'_3$, $R_4$, $R'_4$, $R_5$, and $R'_5$ are each independently hydrogen, hydroxy, formylamino, aminocarbonyl, (aminocarbonyl)amino, aminosulfonyl, or halo; and n and m are each independently an integer from 1 to 10, or its S stereoisomer, or a racemic or non-racemic mixture of isomers thereof, or a pharmaceutically acceptable salt of the compound, its S stereoisomer, or a racemic or non-racemic mixture of isomers thereof.

24. The method of claim 23 wherein $R_1$, $R'_1$, $R_4$, $R'_4$, $R_5$ and $R'_5$ are hydrogen;

each of $R_2$, $R'_2$, $R_3$ and $R'_3$ is independently hydrogen or hydroxy;

R is lower alkyl of 1 to 4 carbon atoms;

n is an integer form 3 to 8; and m is an integer from 1 to 3.

25. The method of claim 24 wherein

R is propyl;

n is 4 or 5; and m is 1.

26. The method of claim 25 wherein the compound is (R)-2-(3,4-dihydroxybenzyl)-1-[5-(N-(2-(3,4-dihydroxyphenyl)ethyl)-N-propylamino)pentyl]pyrrolidine, or a pharmaceutically acceptable salt thereof.

27. The method of claim 25 wherein the compound is (R)-2-(3,4-dihydroxybenzyl)-1-[6(N-(2-(4-hydroxyphenyl)ethyl)-N-propylamino)hexyl]pyrrolidine, or a pharmaceutically acceptable salt thereof.

28. A method of treating hypertension in a mammal, comprising administering to the mammal a pharmaceutically effective amount of a compound of the formula

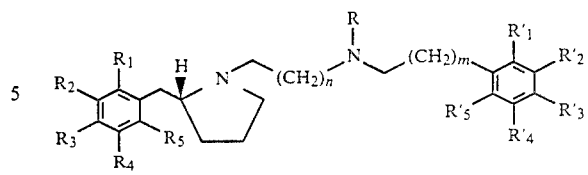

wherein:

R is hydrogen or lower alkyl;

$R_1$, $R'_1$, $R_2$, $R'_2$, $R_3$, $R'_3$, $R_4$, $R'_4$, $R_5$, and $R'_5$ are each independently hydrogen, hydroxy, formylamino, aminocarbonyl, (aminocarbonyl)amino, aminosulfonyl, or halo; and n and m are each independently an integer from 1 to 10, or its S stereoisomer, or a racemic or non-racemic mixture of isomers thereof, or a pharmaceutically acceptable salt of the compound, its S stereoisomer, or a racemic or non-racemic mixture of isomers thereof.

29. The method of claim 28 wherein $R_1$, $R'_1$, $R_4$, $R'_4$, $R_5$ and $R'_5$ are hydrogen;

each of $R_2$, $R'_2$, $R_3$ and $R'_3$ is independently hydrogen or hydroxy;

R is lower alkyl of 1 to 4 carbon atoms;

n is an integer form 3 to 8; and m is an integer from 1 to 3.

30. The method of claim 29 wherein

R is propyl;

n is 4 or 5; and m is 1.

31. The method of claim 30 wherein the compound is (R)-2-(3,4-dihydroxybenzyl)-1-[5-(N-(2-(3,4-dihydroxyphenyl)ethyl)-N-propylamino)pentyl]pyrrolidine, or a pharmaceutically acceptable salt thereof.

32. The method of claim 30 wherein the compound is (R)-2-(3,4-dihydroxybenzyl)-1-[6(N-(2-(4-hydroxyphenyl)ethyl)-N-propylamino)hexyl]pyrrolidine, or a pharmaceutically acceptable salt thereof.

* * * * *